United States Patent [19]

Ehr

[11] Patent Number: 5,347,342
[45] Date of Patent: Sep. 13, 1994

[54] TRANSILLUMINATOR

[75] Inventor: Timothy G. J. Ehr, Menomonee Falls, Wis.

[73] Assignee: Fotodyne Incorporated, Hartland, Wis.

[21] Appl. No.: 40,670

[22] Filed: Mar. 31, 1993

[51] Int. Cl.$^5$ ............................................. G03B 27/04
[52] U.S. Cl. .................................. 355/113; 250/504 R
[58] Field of Search .................... 250/504 R; 355/113, 355/114, 118, 120, 121, 133

[56] References Cited

U.S. PATENT DOCUMENTS 4,560,883 12/1985 Kerchgens ...................... 250/504 R

*Primary Examiner*—Richard A. Wintercorn
*Attorney, Agent, or Firm*—Michael, Best & Friedrich

[57] ABSTRACT

A transilluminator comprising a housing having therein a UV-transmissible window and a UV light source supported within the housing for transmitting UV light through the window. A surface within the housing reflects an image of the light source through the window so that the light source appears at the window to be more than one light source.

17 Claims, 2 Drawing Sheets

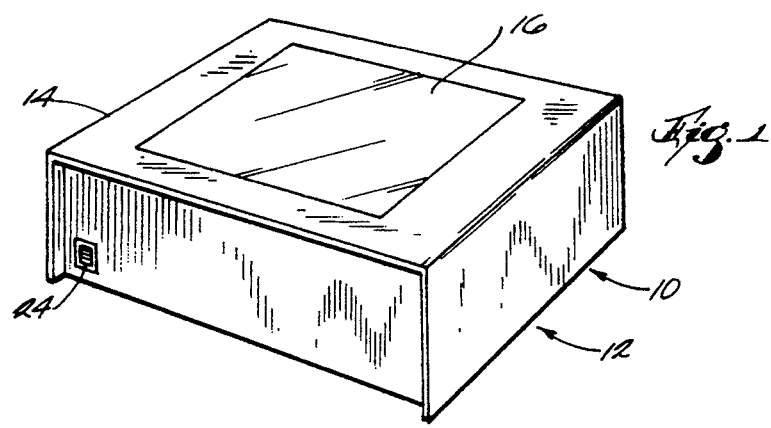
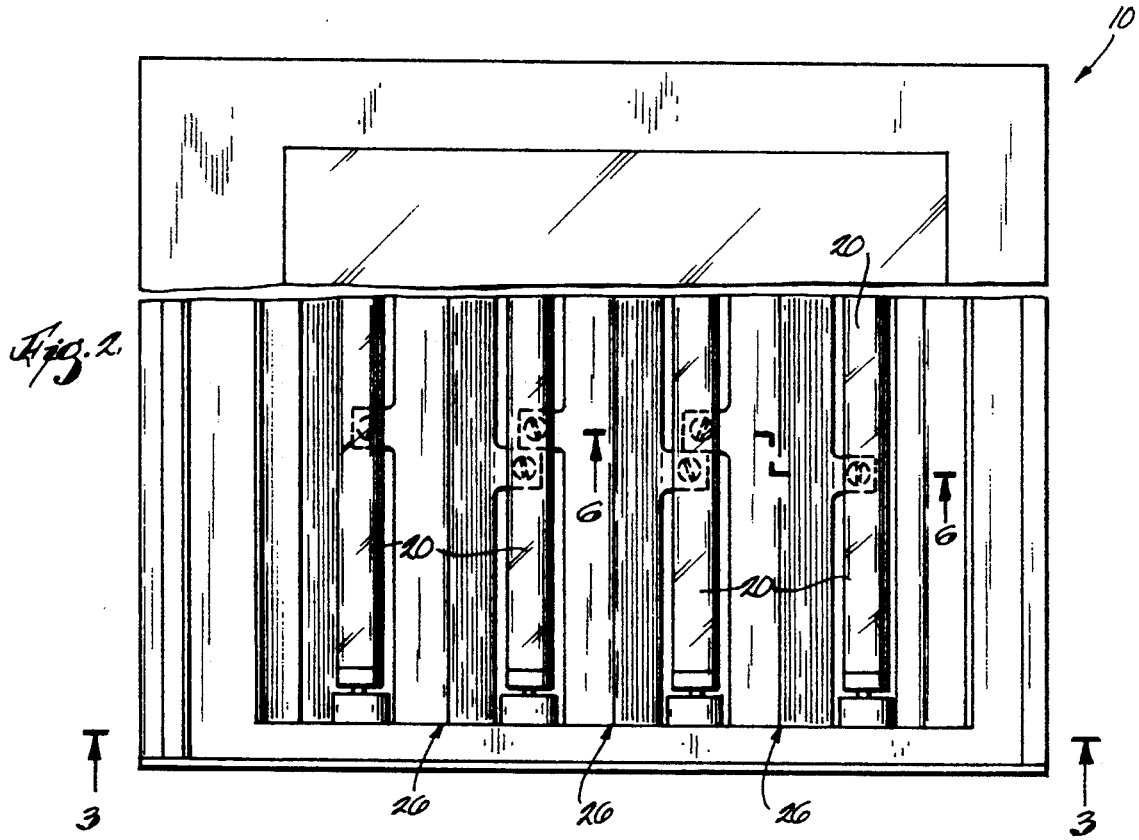
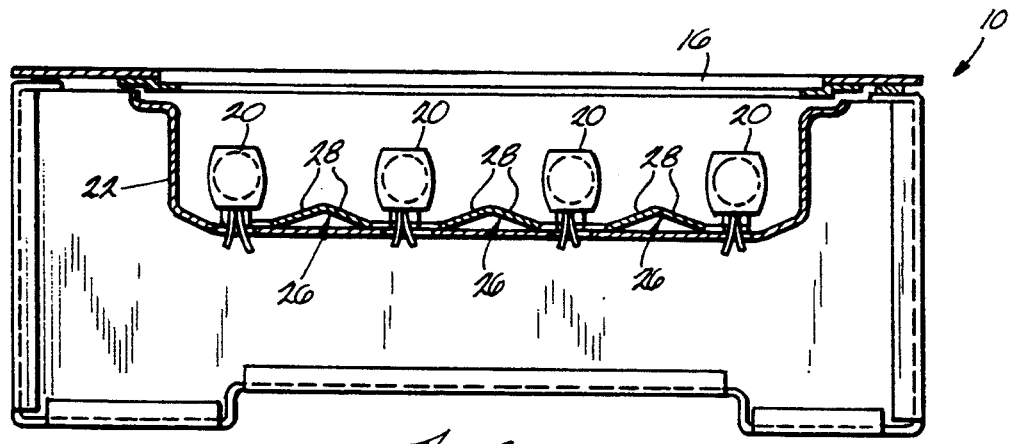

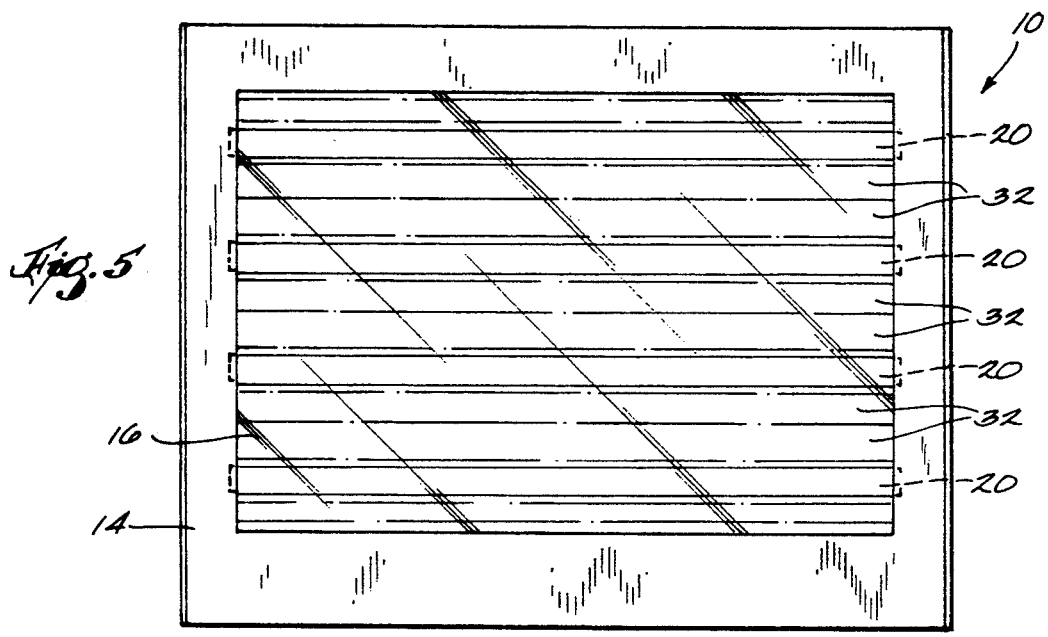
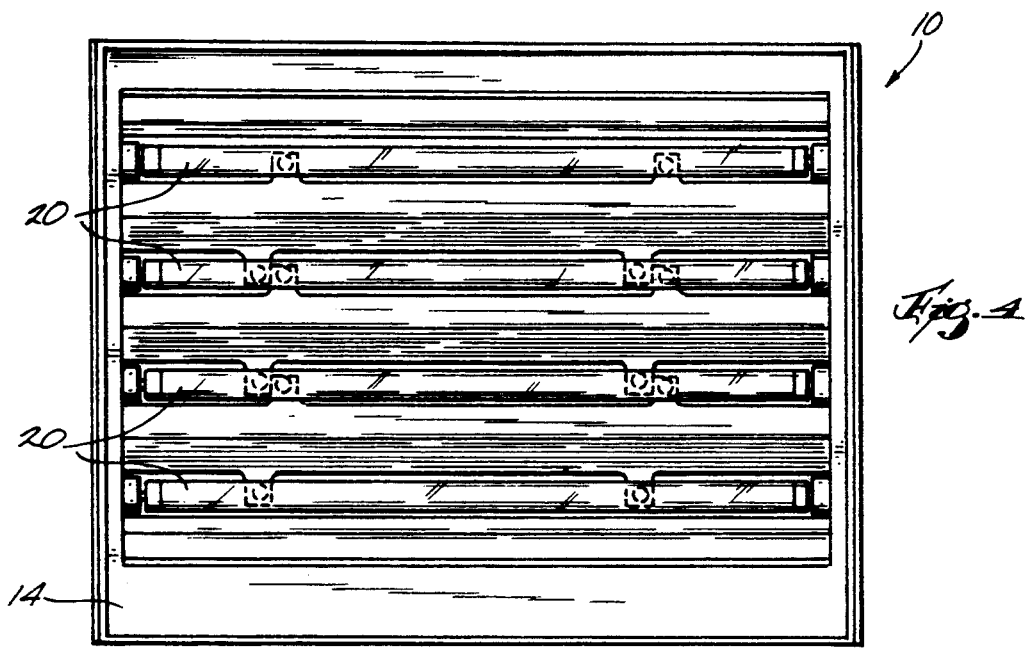
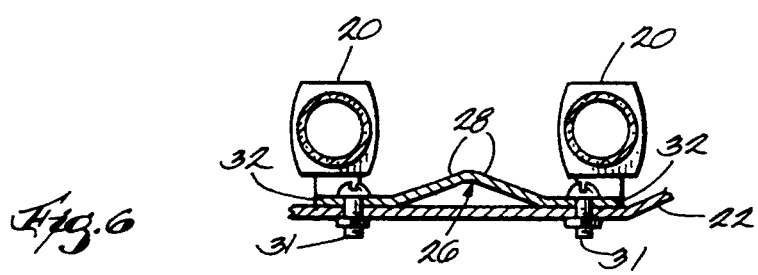

TRANSILLUMINATOR

BACKGROUND OF THE INVENTION

This invention relates to transilluminators for transilluminating electrophoresis gels with ultraviolet light.

A common method for separating, identifying or purifying DNA from a mixed sample is by electrophoresis of the sample through an agarose gel. The electrophoretic migration rate of DNA through agarose gel is dependent upon the molecular weight of the DNA, as well as such considerations as the agarose concentration and the strength of the electric field. The electrophoresis technique is simple and rapid, and results in the formation of distinct bands of DNA within the gel.

After electrophoresis for a sufficient period, electrophoresis gels are typically stained to visualize the bands of DNA, often with low concentrations of the fluorescent dye ethidium bromide. Ethidium bromide which becomes bound-up, or intercalated, between bases of the DNA has an increased fluorescent yield, as compared to free ethidium bromide in solution. Ultraviolet (UV) radiation is absorbed by bound ethidium bromide dye and re-emitted in the red-orange region of the visible spectrum. Thus, the location and relative amount of DNA is detectable by examination of an ethidium bromide-stained electrophoresis gel under illumination by UV light.

One apparatus used to illuminate electrophoresis gels produces UV light in a closed box. A light source within the box transmits UV light through a horizontal window provided in the top of the box. A typical light source is a plurality of parallel fluorescent lamps. The window is typically made of purple filter glass. This filter glass blocks all light except that within a narrow range centered around the specific UV region which creates the above-mentioned fluorescence in the ethidium bromide bound to the DNA. A gel is positioned over the window for illumination by the UV light, which will pass through the window below and illuminate the gel. Such an apparatus is referred to as a transilluminator.

In many applications, the DNA bands within the gel will be further compared and evaluated based on the distance travelled and upon the relative intensity of the fluorescence between bands. These determinations will in turn be somewhat dependent upon the relative strength of the background UV light intensity. The differences in fluorescence of different DNA bands of a given sample, or between a sample and background fluorescence or the fluorescence of trace DNA contaminants can be complicated by the transilluminator's own fluctuations in UV light intensity across the window. For this reason, it is desirable that an even background of UV light be provided for the gel.

SUMMARY OF THE INVENTION

The intensity of UV light at the window will vary depending upon the spacing of the lamps and their location relative to the window. A problem arises when the UV light intensity varies across the window. The interaction of UV light from adjacent lamps can actually cause the relative intensity of UV light above the spaces between lamps to be greater than the light intensity directly above the lamps. This is somewhat counterintuitive, in that the intensity might be expected to be greater over the lamps than over the spaces between the lamps. In any case, peaks and valleys in the intensity of UV light at the window can lead to false readings of the fluorescence of DNA bands in the gel.

A method which could be used to minimize this problem is to use a higher number of UV lamps arrayed closely within the transilluminator beneath the UV filter window. One problem with this approach is the high amount of UV radiation which would be produced. DNA is damaged by UV radiation, and so the overall UV light intensity should be kept at the minimum necessary to cause sufficiently detectable fluorescence of the DNA-bound ethidium bromide dye. An even greater problem is that the excessive use of expensive UV lamps will greatly increase the overall cost of a transilluminator.

The transilluminator of the invention produces even light intensity at the level of the UV filter window by increasing the intensity of UV light at areas having reduced intensity in a conventional transilluminator. In one embodiment, this is accomplished by use of reflecting means within the transilluminator housing. The reflected UV light cooperates with UV light transmitted directly through the window to produce the substantially uniform level of UV light intensity across the UV-transmissible window. For obvious reasons, this desirable effect is preferably maximized slightly above the surface of the purple filter glass, at the level where a gel is placed for transillumination.

In a preferred embodiment the reflecting means comprises reflective surfaces located between lamps. The reflective surfaces are preferably located at opposite sides of and beneath each lamp and slope upwardly and away from the lamp. The reflective surfaces preferably produce, for each UV lamp within the transilluminator, an image of the lamp on either side thereof, so that the appearance to the researcher is a greater number of UV lamps than is actually in the transilluminator. In other words, each light source appears at the window to be more than one light source. The observer sees what appear to be many tightly spaced light sources located within the transilluminator housing.

Other features and advantageous of the invention will become apparent to those skilled in the art upon review of the following description and claims.

BRIEF DESCRIPTION OF THE DRAWINGS

FIG. 1 is a perspective view of a transilluminator embodying the invention.

FIG. 2 is a partially cut away top plan view of the transilluminator (with the front of the transilluminator to the left) showing the UV light sources and reflector elements.

FIG. 3 is view taken along line 3—3 in FIG. 2.

FIG. 4 is a top plan view of the transilluminator with the cover removed.

FIG. 5 is a top plan view of the transilluminator showing the reflected images when the UV light sources are on.

FIG. 6 is a view taken along line 6—6 in FIG. 2.

Before one embodiment of the invention is explained in detail, it is to be understood that the invention is not limited in its application to the details of construction and the arrangement of components set forth in the following description or illustrated in the drawings. The invention is capable of other embodiments and of being practiced or carried out in various ways. Also, it is to be understood that the phraseology and terminology used herein is for the purpose of description and should not be regarded as limiting.

DESCRIPTION OF THE PREFERRED EMBODIMENT

A transilluminator 10 embodying the invention is illustrated in the drawings. The transilluminator 10 generally includes (see FIG. 1) a housing 12 having a horizontal top wall 14. The top wall 14 has therein a UV-transmissible window 16. The window 16 is generally planar and is preferably made of purple filter glass which transmits UV light.

As shown in FIGS. 2–4, a plurality of spaced apart UV light sources 20 are supported within the housing 12 for transmitting UV light through the window 16. The light sources 20 are preferably 8-watt, 300 mm F8T5 fluorescent lamps, although other light sources can be employed. The transilluminator also includes (see FIG. 3) a support pan 22 for securing the UV lamps 20 at a predetermined distance beneath the window 16.

Again referring to FIG. 1, a manual switch 24 is provided on the front of the housing to energize the lamps 20. A cooling fan (not shown) is preferably also incorporated within the housing to prevent thermal damage to the DNA fragments, the agarose gel or other transilluminator components during transillumination.

The transilluminator 10 includes means for reflecting, through the window, UV light generated by the UV lamps 20. While various means may be employed, in the illustrated embodiment (FIGS. 3 and 4) the reflecting means includes, between each pair of adjacent lamps 20, an elongated element 26 having an inverted V-shape in cross section. Each element 26 is parallel to the lamps 20 and provides a reflective surface 28 for each of the adjacent lamps 20. The elements are preferably made of aluminum, and the surfaces 28 are brush finished. Each reflective surface 28 is disposed at an angle that is non-parallel and non-perpendicular with respect to the window 16. In the illustrated embodiment, the reflective surfaces 28 for each lamp 20 are located at opposite sides of and beneath the lamp 20 and slope upwardly and outwardly away from the lamp 20 at an angle of approximately twenty degrees with respect to the window 16. As seen in FIG. 6, the reflective elements 26 are secured to the pan 22 by screws 31 extending through tabs 32 on the reflective elements 26. As seen in FIG. 5, the reflective surfaces 28 reflect an image 32 of each lamp 20 through the window 16 so that each lamp 20 appears at the window 16 to be more than one lamp.

While the UV light sources 20 and the reflective elements 26 are shown as elongated and disposed in parallel relation on the pan 22, other arrangements can be utilized. One such arrangement, not shown, might comprise spherical UV light sources spaced in a grid pattern, each surrounded on four sides by angled reflective elements producing four reflected images per light source.

The reflective surfaces 28 produce a substantially uniform level of UV light intensity across the UV-transmissible window 16. The angle of the reflective surfaces 28 is chosen such that the reflected UV light cooperates with the UV light transmitted directly from the lamps 20 to produce the substantially uniform level of UV light intensity across the UV-transmissible window 16. The reflecting means thereby increases the UV light intensity at portions of the window 16 where the UV light intensity caused by light transmitted directly from the lamps 20 is reduced.

The reflecting means is preferably fine-tuned to maximize even background intensity at or just above the glass 16. Thus, the use of reflective surfaces 28 evens the peaks and valleys of light intensity at the level of the glass 16, thereby solving the problem of having the light intensity greater at the glass directly above the spaces between lamps 20 than at the glass directly above the lamps 20. Adjustments to the level of light intensity at the window 16 can be made by changing the height, location and spacing of the UV lamps 20 and/or the reflective elements 26.

What is claimed is:

1. A transilluminator comprising
   a housing having therein a UV-transmissible window,
   a UV light source supported within said housing for transmitting UV light through said window, and
   means for reflecting an image of said light source through said window so that said light source appears at said window to be more than one light source.

2. A transilluminator as set forth in claim 1 wherein said reflecting means produces a plurality of reflected images of said light source.

3. A transilluminator as set forth in claim 1 comprising a plurality of light sources for transmitting UV light through said window, and means for reflecting an image of each of said light sources through said window.

4. A transilluminator as set forth in claim 1 wherein said UV-transmissible window is generally planar and said reflecting means comprises an element with a reflective surface disposed at an angle that is non-parallel and non-perpendicular with respect to said planar window.

5. A transilluminator as set forth in claim 4 comprising a plurality of light sources for transmitting UV light through said window, and wherein said element is located between and provides a reflective surface for two of said light sources.

6. A transilluminator as set forth in claim 5 wherein said light sources and said element are elongated and disposed in parallel relation within said housing.

7. A transilluminator as set forth in claim 6 wherein said element lies between adjacent light sources and has an inverted V-shape in cross section.

8. A transilluminator comprising
   a housing having therein a UV-transmissible window,
   a light source supported within said housing for producing UV light, and
   means for reflecting through said window UV light produced by said light source, said reflecting means comprising reflective surfaces located at opposite sides of and beneath said light source and sloping upwardly and outwardly away from said light source.

9. A transilluminator as set forth in claim 8 comprising a plurality of light sources for transmitting UV light through said window and including reflective surfaces located at opposite sides of each of said light sources.

10. A transilluminator as set forth in claim 9 wherein reflective surfaces between adjacent light sources form an inverted V-shape in cross section.

11. A transilluminator comprising
    a housing having therein a generally planar UV-transmissible window,
    a plurality of spaced UV light sources supported within said housing for transmitting UV light through said window, and means for producing a substantially uniform level of UV light intensity across said UV-transmissible window.

12. A transilluminator as set forth in claim 11 wherein said means for producing a substantially uniform level of UV light intensity across said window includes means for reflecting through said window light from said plurality of UV light sources such that reflected UV light from said reflecting means cooperates with UV light transmitted directly from said light source through said window to produce said substantially uniform level of UV light intensity across said UV-transmissible window.

13. A transilluminator as set forth in claim 12 wherein said reflecting means increases the UV light intensity at portions of said window where the UV light intensity caused by light transmitted directly from said UV light sources is reduced.

14. A transilluminator as set forth in claim 12 wherein said reflecting means includes reflective surfaces located at opposite sides of each of said light sources.

15. A transilluminator as set forth in claim 14 wherein each of said reflecting surfaces is beneath and slopes upwardly and outwardly away from the associate light source.

16. A transilluminator as set forth in claim 15 wherein reflective surfaces between adjacent light sources form an inverted V-shape in cross section.

17. A transilluminator as set forth in claim 16 wherein said light sources and said reflective surfaces are elongated and disposed in parallel relation within said housing.

* * * * *